(12) United States Patent
Emery (10) Patent No.: US 8,026,731 B1
(45) Date of Patent: Sep. 27, 2011

(54) METHOD AND APPARATUS FOR CONSTRUCTING IMAGES FROM MEASUREMENTS OF IMPEDANCE

(76) Inventor: Jack Scott Emery, Tempe, AZ (US)

( * ) Notice: Subject to any disclaimer, the term of this patent is extended or adjusted under 35 U.S.C. 154(b) by 1194 days.

(21) Appl. No.: 11/738,404

(22) Filed: Apr. 20, 2007

Related U.S. Application Data (60) Provisional application No. 60/794,219, filed on Apr. 20, 2006.

(51) Int. Cl.
*G01R 27/08* (2006.01)
*G01R 27/26* (2006.01)
*G01N 27/02* (2006.01)

(52) U.S. Cl. ........ 324/709; 324/442; 324/444; 324/663; 324/683; 324/693; 324/713

(58) Field of Classification Search .......... 324/709, 324/439, 442, 444, 446, 600, 663, 683, 693, 324/713
See application file for complete search history.

(56) References Cited

U.S. PATENT DOCUMENTS

| | | | | |
|---|---|---|---|---|
| 4,288,741 A | * | 9/1981 | Dechene et al. | 324/664 |
| 5,103,181 A | * | 4/1992 | Gaisford et al. | 324/637 |
| 5,560,372 A | * | 10/1996 | Cory | 600/547 |
| 6,784,672 B2 | * | 8/2004 | Steele et al. | 324/663 |
| 6,962,079 B2 | * | 11/2005 | Eguchi et al. | 73/304 R |
| 6,978,170 B1 | * | 12/2005 | Onda et al. | 600/547 |
| 7,283,869 B2 | * | 10/2007 | Onda et al. | 600/547 |
| 2003/0050570 A1 | * | 3/2003 | Kodama | 600/547 |
| 2004/0077969 A1 | * | 4/2004 | Onda et al. | 600/547 |
| 2006/0085049 A1 | * | 4/2006 | Cory et al. | 600/547 |
| 2006/0247543 A1 | * | 11/2006 | Cornish et al. | 600/547 |

* cited by examiner

*Primary Examiner* — Timothy J Dole
(74) *Attorney, Agent, or Firm* — Jack S. Emery (57) ABSTRACT

Apparatus and methods are disclosed for obtaining an image of the impedance properties of an object by inferring a measure of straight-line path impedance along a plurality of paths from a plurality of current amplitude and phase measurements made between combinations of electrodes placed at selected points, and/or from measurements of the intensity of the electromagnetic signal emitted when an alternating current is made to resonate along the straight line path.

9 Claims, 5 Drawing Sheets

Figure 5

METHOD AND APPARATUS FOR CONSTRUCTING IMAGES FROM MEASUREMENTS OF IMPEDANCE

CROSS-REFERENCE TO RELATED APPLICATIONS

This application claims the benefit of U.S. Provisional Application No. 60/794,219 filed Apr. 20, 2006.

STATEMENT REGARDING FEDERALLY SPONSORED RESEARCH & DEVELOPMENT

Not applicable

BACKGROUND

Description of Prior Art

Many investigators have attempted to devise methods for producing images corresponding to the electrical impedance properties of a two or three dimensional object based upon measurements taken from electrodes placed around the outside of (and/or, optionally, at selected points within) the object. Potential applications of such a technology (referred to as electrical impedance tomography, or 'EIT') include medical imaging and diagnosis, and geological profiling.

Prior art approaches to the problem have typically involved passing currents between various pairs of electrodes arrayed around the periphery of the object to be imaged. Multiple frequencies may be employed, and/or currents may be passed through multiple electrodes at once. Thus far, however, there has been relatively little success in reconstructing meaningful and reproducible images at a useful resolution, because of a seemingly intractable problem: currents applied through electrodes follow multiple paths of least resistance that themselves depend on the impedance characteristics of the object and are therefore unpredictable. Because of this, impedance imaging is in principle unlike other kinds of imaging such as computed tomography, where the measured signal represents an integral of the property being measured (typically density to x-rays) along a straight line path, which allows for straightforward reconstruction of a unique image from a number of such measurements along a variety of paths. In computed tomography where the measured data consists of line integrals of some physical property, reconstruction is accomplished using techniques that are well known to persons having ordinary skill in the art of imaging, such as back projection or Fourier analysis. Because the measurements sought to be used for impedance imaging are not line integrals, but rather represent the effect of the impedance properties of the object to be imaged along many paths at once, the problem of reconstructing an image from impedance measurements (often referred to as the 'inverse EIT problem') is one of a class of inverse problems known to be highly non-linear, extremely ill-posed, and having many local optima.

Prior art efforts to obtain useful images despite these drawbacks have typically focused on seeking ways to make the reconstruction problem less intractable—for example, in physiological imaging, the analysis may begin with an assumed mapping of the typical impedance properties and topography of the anatomical region sought to be measured. It may then be possible to construct an image at some resolution by using the assumed mapping to predict the path distribution of the applied currents, and use the results of the measurements to iteratively improve the mapping.

The present invention takes a different approach: it seeks to make measurements in such a way that the current along a straight line path between electrodes can be estimated, thereby providing line integrals from which images can be reconstructed directly using any of the many well-known line integral-based image reconstruction methods.

SUMMARY OF THE INVENTION

The present invention offers an improved system and method (and computing apparatus and measurement apparatus implementing such method) for obtaining an image of the impedance properties of an object from a plurality of current measurements made between combinations of electrodes placed at selected points, typically around the periphery of the object but also optionally within the interior of the object. The measurements in question are able to estimate a measure of the impedance along a straight line path between electrodes by taking advantage of either or both of two novel improvements, described in detail infra: (1) the use of the phase shifts and current amplitudes measured at a plurality of frequencies, together with knowledge of the distance between electrodes, to determine the part of the current attenuation attributable to the straight line path, and/or (2) the use of a calibrated frequency to produce a standing wave along the straight line path, thereby, in effect, interrogating the straight line path with a signal that is resonant along that path.

BRIEF DESCRIPTION OF THE DRAWINGS

Reference will be made to the accompanying drawings, which illustrate non-limiting examples, embodiments, and/or aspects of the invention.

DETAILED DESCRIPTION OF THE INVENTION

The motivation of the method and apparatus described here is to solve the problem of the fundamental intractability of the impedance imaging problem by obtaining measurements from which line integrals, or at least bounded estimates of line integrals, of impedance properties can be obtained. Current passed between electrodes follows multiple paths, and there is no known reliable technique for physically confining the electrical current to a predetermined path, so in order to obtain line integral measurements, it is necessary to invent a way of determining which part of the injected current did in fact follow the straight line path. The discussion to follow will describe a system and method for making that determination, involving several related techniques that can be used separately or together and that enable the present invention.

Figure 1:
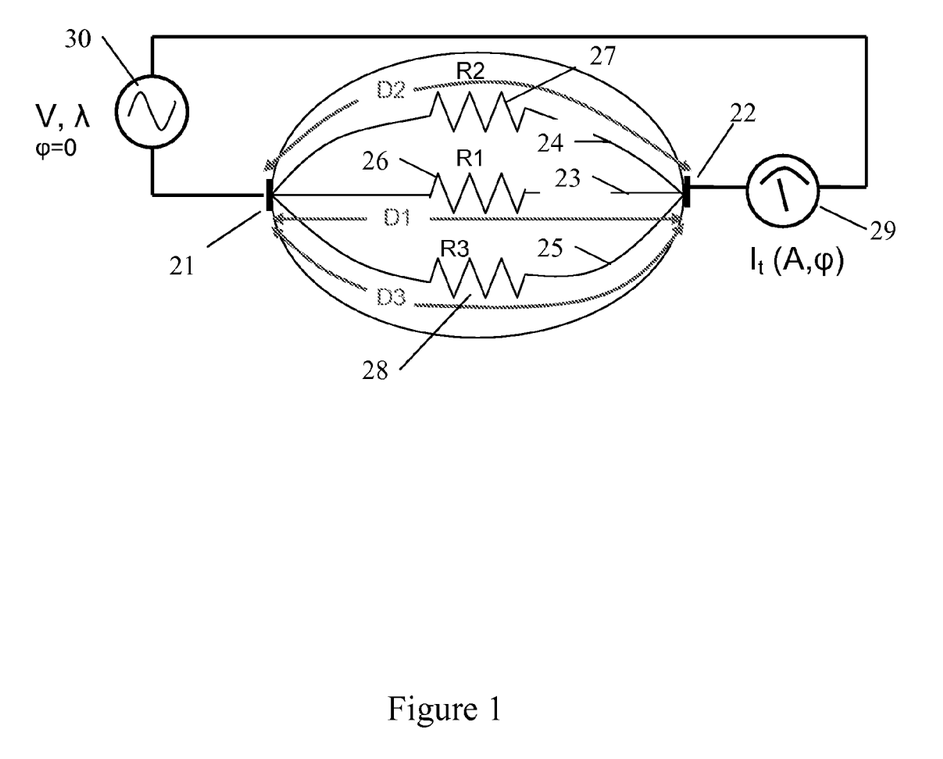
FIG. 1 illustrates the modeling of impedance properties of an object for computational purposes.

Determination of Line Integral Impedance Properties from Amplitude and Phase Shift Measurements at Multiple Frequencies Consider an alternating current signal of predetermined frequency 30 applied between two electrodes placed on the periphery of an object to be imaged 21, 22, as shown in FIG. 1. The resistance properties of the object can be approximated by an array of parallel resistors $R_1$ 26, $R_2$ 27, and $R_3$ 28 as shown, each on a separate circuit branch 23, 24, 25 respectively, which branches are of length $D_1$, $D_2$, and $D_3$ respectively. (The approximation can be improved using a larger number of parallel paths; in this illustration only three are shown, for simplicity. The system and method described is generalizable to any number of paths. Capacitance and inductance effects are also ignored in this example for simplicity, as are resonant effects; these will be discussed infra.) If a sinusoidal signal at a fixed frequency f and specified potential V (herein referred to as an "interrogation signal") is applied across the electrodes 21 and 22, alternating currents will be produced in each of the circuit branches 23, 24, 25, and these alternating currents will superpose at the 'downstream' electrode 22, producing a composite current signal, still of frequency f but, in general, shifted in phase and attenuated in amplitude from the 'upstream' current at the electrode 21. This phase shift and attenuation occurs because all branches except the straight line path 23 are longer than the straight line path, so the signals on the non-straight line paths (hereinafter referred to as the shunt paths) are relatively delayed in their arrival at the 'downstream' electrode 22 by an amount of time that varies according to the ratio of the shunt path length to the straight line path length. Thus when the signals from the several branches superpose at the 'downstream' electrode, they interfere destructively to a greater or lesser degree, causing the downstream current to be attenuated and phase shifted. (This result may seem counterintuitive, since the usual principles of circuit analysis would require the 'upstream' current to equal the 'downstream' current. However, the usual principles of circuit analysis do not take into account propagation delay due to the differences in path length, since the attenuation and phase shift is negligible at the frequencies usually analyzed, which correspond to wavelengths that are large relative to the path lengths. Note: as used herein, two or more signals are said to interfere constructively if and only if they are in phase, so that the amplitude of the signal obtained by superposing them is equal to the sum of the amplitudes of the separate signals. They are said to interfere destructively if any of the signals being superposed is out of phase to any significant degree, in which case the amplitude of the signal obtained by superposing them will always be less than the sum of the amplitudes of the separate signals.)

The attenuation and phase shift caused by the interference of the signals traveling along the various paths can be used to infer the amplitude of the individual path currents, in the manner disclosed herein. In general, doing so requires knowledge of (1) the fixed potential of each applied interrogation signal, (2) the lengths of each of the current paths, and (3) the amplitude of the current at the 'downstream' electrode and the phase of that current relative to the applied signal or some other datum, with measurements taken at a number of fixed frequencies at least equal to the number of paths to be evaluated. The discussion to follow will first describe how this may be done in the context of the simplified model of FIG. 1, then discuss how the model may be generalized to the problem of estimating the impedance along straight line paths through two or three dimensional objects.

Consider an alternating current signal of fixed potential V and frequency $f_1$ applied across electrodes 21 and 22 in FIG. 1. A current $I_{1,1}$ will be produced in the straight line path 23 equal to $V/R_1$ and will be phase shifted relative to the applied signal by an angle in radians equal to $2\pi(D_1-\lambda_1)/\lambda_1$, where $\lambda_1$ is the wavelength corresponding to $f_1$ and given by $\lambda_1 = c/f$ where c is the speed of light in the medium through which the current is passing. A current $I_{1,2}$ equal to $V/R_2$ will be produced in the shunt path 24, and will be phase shifted relative to $I_1$ by an amount equal to $2\pi(D_2-\lambda_1)/\lambda_1$. Similarly, A current $I_{1,3}$ equal to $V/R_3$ will be produced in the shunt path 25, and will be phase shifted relative to $I_1$ by an amount equal to $2\pi(D_3-\lambda_1)/\lambda_1$. (For consistency, a current $I_{x,y}$ will be taken throughout this written description to mean the current in branch y due to application of frequency $f_x$. A current $I_x$ will be taken to refer to the aggregate superposed current from all paths measured at the downstream electrode due to application of frequency $f_x$.)

It is convenient to represent these currents $I_{1,1}, I_{1,2}, I_{1,3}$ in complex form as $(V/R_1) \cos(2\pi(D_1-\lambda_1)/\lambda_1)+j$ $((V/R_1) \sin(2\pi(D_2-\lambda_1)/\lambda_1))$, $(V/R_2) \cos(2\pi(D_2-\lambda_1)/\lambda_1)+j$ $((V/R_2) \sin(2\pi(D_2-\lambda_1)/\lambda_1))$, and $(V/R_3) \cos(2\pi(D_3-\lambda_1)/\lambda_1)+j$ $((V/R_3) \sin(2\pi(D_3-\lambda_1)/\lambda_1))$, respectively, where j is the square root of minus one. The measured total current $I_1$ obtained by making a current measurement 29 at the downstream electrode 22 after applying frequency $f_1$ will be given by the sum of these three complex values.

The analysis of the preceding two paragraphs can be repeated at two additional frequencies $f_2$ and $f_3$, corresponding to additional wavelengths $\lambda_2$ and $\lambda_3$, and giving branch currents in circuit branches 23, 24, 25 of $(V/R_1) \cos(2\pi(D_1-\lambda_2)/\lambda_2)+j$ $((V/R_1) \sin(2\pi(D_2-\lambda_2)/\lambda_2))$, $(V/R_2) \cos(2\pi(D_2-\lambda_2)/\lambda_2)+j$ $((V/R_2) \sin(2\pi(D_2-\lambda_2)/\lambda_2))$, and $(V/R_3) \cos(2\pi(D_3-\lambda_2)/\lambda_2)+j$ $((V/R_3) \sin(2\pi(D_3-\lambda_2)/\lambda_2))$, respectively, when the signal at frequency $f_2$ is applied, and $(V/R_1) \cos(2\pi(D_1-\lambda_3)/\lambda_3)+j$ $((V/R_1) \sin(2\pi(D_2-\lambda_3)/\lambda_3))$, $(V/R_2) \cos(2\pi(D_2-\lambda_3)/\lambda_3)+j$ $((V/R_2) \sin(2\pi(D_2-\lambda_3)/\lambda_3))$, and $(V/R_3) \cos(2\pi(D_3-\lambda_3)/\lambda_3)+j$ $((V/R_3) \sin(2\pi(D_3-\lambda_3)/\lambda_3))$, respectively, when the signal at frequency $f_3$ is applied. Again, the branch currents, expressed in complex form, may be summed to give the currents $I_2$ and $I_3$ that will be measured at the downstream electrode 22.

The relations described in the three preceding paragraphs comprise a linear system as follows:

$$\frac{I_1}{V} = \left(\frac{1}{R_1}\right)\left(\cos\left(2\pi\frac{(D_1-\lambda_1)}{\lambda_1}\right) + j \cdot \sin\left(2\pi\frac{(D_1-\lambda_1)}{\lambda_1}\right)\right) +$$
$$\left(\frac{1}{R_2}\right)\left(\cos\left(2\pi\frac{(D_2-\lambda_1)}{\lambda_1}\right) + j \cdot \sin\left(2\pi\frac{(D_2-\lambda_1)}{\lambda_1}\right)\right) +$$
$$\left(\frac{1}{R_3}\right)\left(\cos\left(2\pi\frac{(D_3-\lambda_1)}{\lambda_1}\right) + j \cdot \sin\left(2\pi\frac{(D_3-\lambda_1)}{\lambda_1}\right)\right),$$

$$\frac{I_2}{V} = \left(\frac{1}{R_1}\right)\left(\cos\left(2\pi\frac{(D_1-\lambda_2)}{\lambda_2}\right) + j \cdot \sin\left(2\pi\frac{(D_1-\lambda_2)}{\lambda_2}\right)\right) +$$
$$\left(\frac{1}{R_2}\right)\left(\cos\left(2\pi\frac{(D_2-\lambda_2)}{\lambda_2}\right) + j \cdot \sin\left(2\pi\frac{(D_2-\lambda_2)}{\lambda_2}\right)\right) +$$
$$\left(\frac{1}{R_3}\right)\left(\cos\left(2\pi\frac{(D_3-\lambda_2)}{\lambda_2}\right) + j \cdot \sin\left(2\pi\frac{(D_3-\lambda_2)}{\lambda_2}\right)\right),$$

$$\frac{I_3}{V} = \left(\frac{1}{R_1}\right)\left(\cos\left(2\pi\frac{(D_1-\lambda_3)}{\lambda_3}\right) + j \cdot \sin\left(2\pi\frac{(D_1-\lambda_3)}{\lambda_3}\right)\right) +$$
$$\left(\frac{1}{R_2}\right)\left(\cos\left(2\pi\frac{(D_2-\lambda_3)}{\lambda_3}\right) + j \cdot \sin\left(2\pi\frac{(D_2-\lambda_3)}{\lambda_3}\right)\right) +$$
$$\left(\frac{1}{R_3}\right)\left(\cos\left(2\pi\frac{(D_3-\lambda_3)}{\lambda_3}\right) + j \cdot \sin\left(2\pi\frac{(D_3-\lambda_3)}{\lambda_3}\right)\right),$$

The quantities $1/R_1$, $1/R_2$, $1/R_3$ may therefore be determined by solving the foregoing linear system, using any of the many techniques for solving linear systems that are known to persons having ordinary skill in the art of linear mathematics, such as, by way of example only, Gaussian elimination or matrix inversion. To do this it is merely necessary to know V, which in the case of actual physical measurement is known because it is the fixed voltage applied; $I_1$, $I_2$, and $I_3$, which are known by measuring the current amplitudes and phases directly using a suitable instrument 29 at the downstream electrode 22 upon applying frequencies corresponding to wavelengths $\lambda_1$, $\lambda_2$, and $\lambda_3$; the path lengths $D_1$, $D_2$, and $D_3$, which in this example are given and in the context of an actual measurement on an object would be determined by direct measurement of the straight line distance $D_1$ between electrodes and choosing suitable arbitrary values for $D_2$ and $D_3$ as described infra; and the wavelengths $\lambda_1$, $\lambda_2$, and $\lambda_3$, which may be determined from the known frequencies applied, assuming the speed of light in the medium is known (and if not it can be measured or estimated).

The linear system can be expressed in matrix form and generalized to any arbitrary number of resistance paths and interrogating signal wavelengths, as follows:

$$\left(\frac{I_n}{V_n}\right) = \left(\cos\left(2\pi\frac{(D_m - \lambda_n)}{\lambda_n}\right) + j \cdot \sin\left(2\pi\frac{(D_m - \lambda_n)}{\lambda_n}\right)\right)\left(\frac{1}{R_m}\right)$$

where $$\left(\frac{I_n}{V_n}\right)$$

is a column vector of n observed currents (scaled by the applied voltage amplitude, which can optionally be different for each frequency, hence the subscript), expressed in polar form, at the downstream electrode upon applying an alternating current at potential V and frequencies $f_1 \ldots f_n$ corresponding to wavelengths in the medium being interrogated of $\lambda_1 \ldots \lambda_n$;

$$\left(\frac{1}{R_m}\right)$$

is a column vector of the m resistances in paths $1 \ldots m$; and $$\left(\cos\left(2\pi\frac{(D_m - \lambda_n)}{\lambda_n}\right) + j \cdot \sin\left(2\pi\frac{(D_m - \lambda_n)}{\lambda_n}\right)\right)$$

is a n (rows) by m (columns) matrix of coefficients corresponding to the phase shift attributable to the difference between the path length along path m and the wavelength $\lambda_n$ of the applied signal. The number of different interrogating frequencies n must be chosen to be at least equal to the number of paths to be evaluated m; if the number of frequencies n is less than the number of paths m, the system will in general be underdetermined, and if the number of frequencies n exceeds the number of paths m, the system will in general be overdetermined. In the latter case, use may be made of various techniques known to persons having ordinary skill in the art of linear mathematics for improving the accuracy of the solution by utilizing the additional information embodied in the constraints exceeding the number of degrees of freedom of the system.

Extending the Model to Account for Capacitance

Figure 2:
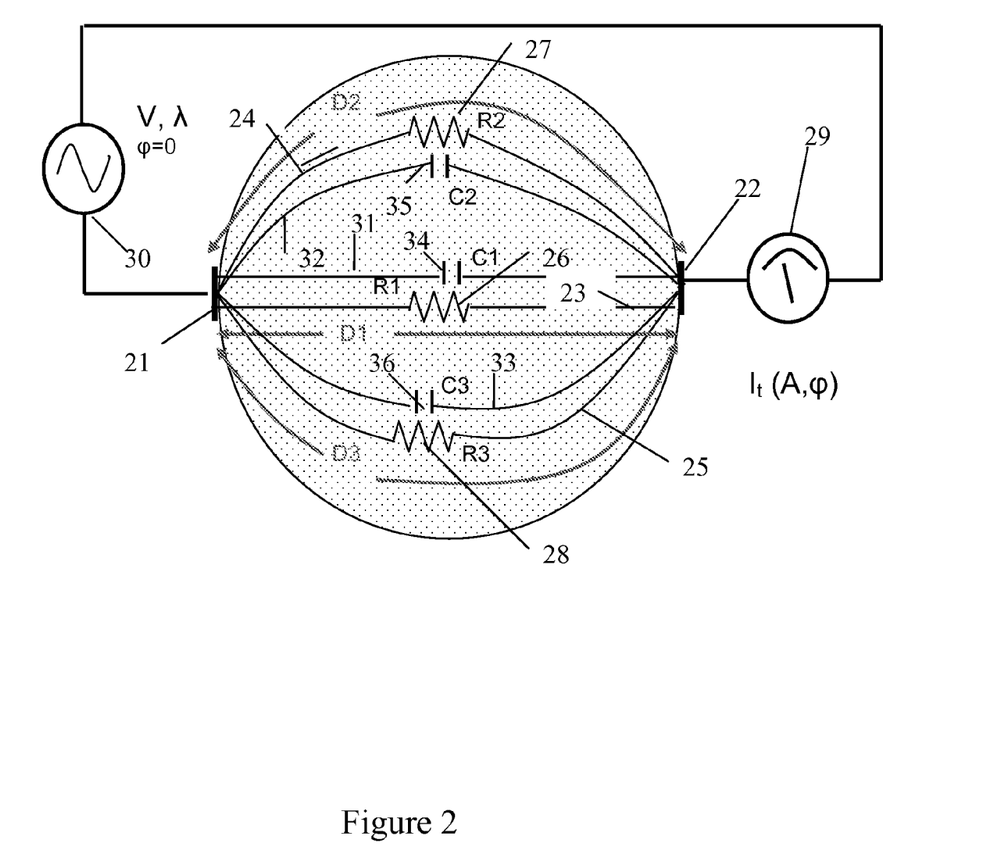
FIG. 2 illustrates the modeling of impedance properties of an object for computational purposes taking into account capacitance.

The foregoing system and method can be extended to account for capacitance effects by including capacitance branches, as shown with respect to the three-branch example in FIG. 2. Capacitances of the three branches are represented by three additional parallel paths 31, 32, 33 having capacitances, respectively, of $C_1$, $C_2$, and $C_3$ and having lengths $D_1$, $D_2$, and $D_3$, respectively, identical to those of the corresponding resistance paths. In effect, each of the three paths is treated as a parallel RC path, and represented as two separate paths, one a pure resistance path, and one a pure capacitance path. The current due to a sinusoidal voltage signal through a capacitance is inversely proportional to the capacitive reactance, $$\frac{1}{2\pi f C} = \frac{\lambda}{2\pi c C},$$

where f is the frequency of the signal, C is the capacitance, $\lambda$ is the wavelength of the signal, and c is the speed of light in the medium through which the signal is passing. According, the expected path current I at the downstream electrode for a path with capacitance C, path length D, at interrogation wavelength $\lambda$ is given by $$I(\lambda, D, C) = V \cdot jC \cdot \left(\frac{2\pi c}{\lambda}\right)\left(\cos\left(2\pi\frac{(D-\lambda)}{\lambda}\right) + j \cdot \sin\left(2\pi\frac{(D-\lambda)}{\lambda}\right)\right)$$

The coefficient, $$\left(\frac{2\pi c}{\lambda}\right)\left(\cos\left(2\pi\frac{(D-\lambda)}{\lambda}\right) + j \cdot \sin\left(2\pi\frac{(D-\lambda)}{\lambda}\right)\right),$$

depends only on D and $\lambda$ (making the assumption that c is known or can be estimated or measured and that the medium is isotropic regarding c along the path in question). Therefore, the linear system describing the currents measured at the downstream electrode 22 (see FIG. 2) is given by:

$$\left(\frac{I_n}{V_n}\right) = \left\{\left(\cos\left(2\pi\frac{(D_m - \lambda_n)}{\lambda_n}\right) + j \cdot \sin\left(2\pi\frac{(D_m - \lambda_n)}{\lambda_n}\right)\right),\right.$$
$$\left.\left(\frac{2\pi c}{\lambda_n}\right)\left(\cos\left(2\pi\frac{(D_m - \lambda_n)}{\lambda_n}\right) + j \cdot \sin\left(2\pi\frac{(D_m - \lambda_n)}{\lambda_n}\right)\right)\right\}\left\{\begin{array}{c}\frac{1}{R_m},\\ jC_m\end{array}\right\}$$

Where $$\left(\frac{I_n}{V_n}\right)$$

is again a vector of measured currents upon applying sinusoidal voltage signals of amplitude $V_1 \ldots V_n$ and wavelengths $\lambda_1 \ldots \lambda_n$ between electrodes 21 and 22 (such currents expressed in complex form); the matrix of coefficients $$\left\{\left(\cos\left(2\pi\frac{(D_m - \lambda_n)}{\lambda_n}\right) + j \cdot \sin\left(2\pi\frac{(D_m - \lambda_n)}{\lambda_n}\right)\right),\right.$$
$$\left.\left(\frac{2\pi c}{\lambda_n}\right)\left(\cos\left(2\pi\frac{(D_m - \lambda_n)}{\lambda_n}\right) + j \cdot \sin\left(2\pi\frac{(D_m - \lambda_n)}{\lambda_n}\right)\right)\right\}$$

is a n (rows) by 2m (columns) matrix of coefficients, in alternating columns as shown, with the odd numbered col umns corresponding to resistance paths and determined according to the expression $$\left(\cos\left(2\pi\frac{(D_m - \lambda_n)}{\lambda_n}\right) + j \cdot \sin\left(2\pi\frac{(D_m - \lambda_n)}{\lambda_n}\right)\right),$$

and the even numbered columns corresponding to capacitance paths and determined according to the expression $$\left(\frac{2\pi c}{\lambda_n}\right)\left(\cos\left(2\pi\frac{(D_m - \lambda_n)}{\lambda_n}\right) + j \cdot \sin\left(2\pi\frac{(D_m - \lambda_n)}{\lambda_n}\right)\right);$$

and $$\left\{\begin{array}{c} \frac{1}{R_m}, \\ jC_m \end{array}\right\}$$

is a vector of unknown values of $1/R_m$ and $jC_m$ to be solved for, with the odd numbered rows representing $1/R_m$ values and the even numbered rows representing $jC_m$ values. The $C_m$ values (or, alternatively, the matrix coefficients for the even numbered columns) are multiplied by j so as to account for the 90 degree phase shift caused by the capacitance. A Mathematica program implementing the foregoing methods and illustrating the 3-resistance path, 3-capacitance path example using specific numeric values follows as Appendix A. The values shown therein are not intended to be physiologically realistic, but merely to illustrate the application of the method and show how it may be implemented in software.

Inductance is usually thought to be negligible in physiological media, and has not been accounted for in the foregoing example. It will be apparent, however, that the model is easily extended to account for inductance by including additional paths for the inductances in the same manner as has been done for the capacitances, and including appropriate coefficients taking into account inductive reactance and the 90 degree phase shift caused by inductance in the opposite direction from the phase shift caused by capacitance. Doing so would obviously necessitate interrogating at a number of additional frequencies at least equal to the number of inductance paths added.

The model described above and illustrated in the example can be generalized to any arbitrary number of paths, limited only by the number of interrogation frequencies applied, the computational resources available to handle the large matrices that result from large numbers of paths, and the ability to measure currents with sufficient accuracy.

Application of System and Method as to Continuous Medium

Obviously, the foregoing example, dealing as it does with a finite number of discrete paths, differs from the type of measurement desired for imaging purposes, where the conductive properties of the object being measured are continuous. To understand how the system and method of the invention may be used for estimating the impedance of a continuous two or three dimensional object along a straight line path between two electrodes, it will be convenient to consider the configuration shown in FIG. 3. Any predetermined group of paths 37 (referred to herein as 'component paths') may in principle be represented in the model by a single path 38 (referred to herein as a 'lumped path'). If this is done, the lumped path values determined by the model will always underestimate the aggregate of the composite path currents, and therefore overestimate the impedance. This is so because the component paths are of unequal lengths. Therefore the currents on such component paths are delayed relative to the interrogation signal by varying time intervals in their arrival at the downstream electrode 22, so they are out of phase with each other to varying degrees. The 'true' aggregate current representing the true impedances of the component paths is the in-phase sum of all the component path currents represented by the 'lumped' path; to the extent that any of the component path currents is out of phase with the others, the aggregate current must be reduced from the 'true' aggregate current when the component path currents are superposed.

Figure 3:
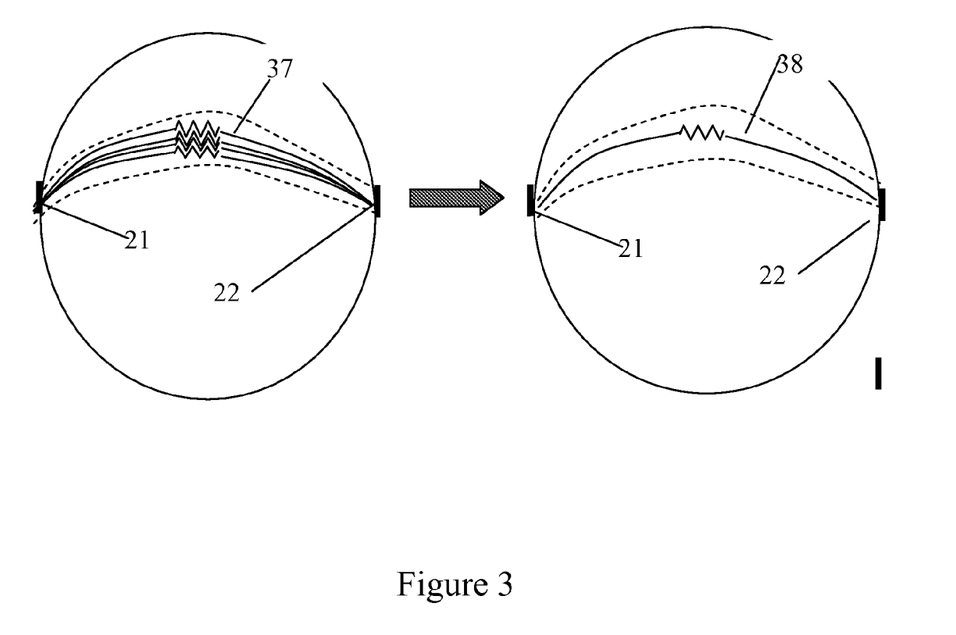
FIG. 3 illustrates the modeling of impedance properties of a region by a single lumped impedance.

The extent to which the 'lumped' shunt path current underestimates the 'true' aggregate of the currents on the paths represented by the 'lumped' shunt path depends upon the distribution of the path lengths of such paths. In general, the narrower the distribution of path lengths of the component paths 37, so that the variation in path length among the component paths is relatively small, then the smaller will be the difference between the 'true' aggregate current and the lumped path current obtained by the model. If the distribution of the component paths is known or can be estimated, then it is possible to compute a correction factor for the average expected error based on the attenuation to be expected given the distribution of paths present, the interrogation frequency, and an assumed distribution of current amplitudes among the component paths.

For imaging purposes, therefore, a somewhat crude measure of the straight line path impedance can be obtained using the analysis described herein with only two paths: the straight line path for which the path length $D_1$ is measured directly as the distance between electrodes; and a single shunt path, whose path length $D_2$ is determined arbitrarily as a reasonable 'lumped' shunt path based on the known geometry of the object being imaged. For example, for an object that is approximately symmetrical about the straight line path, any path coplanar with the straight line path and equidistant between the straight line path and the boundary of the object might reasonably be taken as the lumped shunt path. A minimum of four interrogation signals at different frequencies is applied to the electrodes in the manner already described, and, for each frequency, the current amplitude and phase is measured at the downstream electrode and, for convenience, converted to a complex value. The linear system described herein is solved and the straight line path resistance and capacitance are computed. The procedure is repeated for a plurality of other electrode pair locations. From the resistance (and optionally capacitance) values obtained for the various straight line paths, an image may be constructed by any of the well known methods for constructing an image from line integrals, such as back projection or Fourier analysis.

A Preferred Embodiment

Because the expected underestimation of currents depends upon the range of path lengths represented by the lumped paths, it is desirable to reduce the range of path lengths of the component paths corresponding to each lumped path as much as possible. Therefore, a preferred embodiment of the system and method of the invention proceeds, in general, as follows: First, a plurality of electrode pair placements is determined, in such a way that the straight line paths between the chosen electrode pair positions are spatially distributed in a manner suitable for image reconstruction by back projection when the impedances of such straight line paths have been determined, at the desired resolution.

Then, for each electrode position pair so determined, the impedance properties of the paths between the two electrodes are determined using the methods described herein, and in general as described in this paragraph. First, unless it is known a priori, the distance $D_1$ between the two electrodes is measured using a caliper. (As used herein, "caliper" shall mean any apparatus now known or existing at any future time, and any equivalent thereof, whose function is to measure the straight line distance between two points in space.) A distance $D_{MAX}$, being the longest current path to be analyzed, is also determined by measuring or estimating the longest distance between the two electrodes along the circumference of the object being imaged, and coplanar with the straight line path. (It is recognized that, in theory, current can take convoluted paths that could be much longer than a direct circumferential path, but it is believed that as a practical matter the currents attributable to extremely long paths may reasonably be neglected for imaging purposes. The determination of $D_{MAX}$ can be made in many possible ways; the method described is merely one preferred method.) It is then necessary to determine the number of shunt paths to be analyzed, which also determines the number of interrogation frequencies to be applied. In this preferred embodiment, approximately 100 shunt paths is considered a suitable number; taking into account capacitance paths, this results in a linear system of rank approximately 200, which is readily and quickly solvable on a typical personal computer using appropriate software. The lengths of the assumed shunt paths are distributed evenly over the range from $D_1$ and $D_{MAX}$, inclusive. Interrogation frequencies are then selected. The number of frequencies must at least equal the number of path lengths; it is recommended that a larger number be used, in case any readings must be discarded on account of error or in case it is desired to select those frequencies that best optimize the conditioning of the coefficient matrix. Selection of the frequency range depends upon several competing considerations. Interrogation signals of shorter wavelengths are desirable from the standpoint of giving larger relative phase shifts between paths, making the system less sensitive to measurement error. However, very short wavelengths (i.e. in the microwave range) do not propagate well in tissue, cause local heating effects, and may cause artifacts if the difference between the lengths of any two paths is greater than half the wavelength, since in that case the two currents shift in phase with respect to each other enough to return to more or less in-phase alignment. It is believed that for purposes of physiological imaging, interrogation signal wavelengths ranging from on the order of a minimum ($\lambda_{MIN}$) approximately three or four times $D_{MAX}$ to a maximum ($\lambda_{MAX}$) of approximately 20 times $D_{MAX}$ represent an appropriate compromise for this preferred embodiment. The invention is not, however, limited to such frequencies, and, as is apparent from the discussion above, in principle any frequencies can be used. The desired number of interrogation wavelengths may be distributed evenly over the range from $\lambda_{MIN}$ to $\lambda_{MAX}$; it may also be deemed desirable to then adjust each of these evenly distributed wavelengths by a small random factor so as to avoid wavelengths that are even multiples of other wavelengths. This adjustment is believed to possibly improve the conditioning of the coefficient matrix. A steady state sinusoidal signal of constant voltage amplitude at each interrogation frequency is applied in turn at one of the electrodes, and the amplitude and phase of the current is measured at the other electrode, in the general manner shown in FIG. 2 and described above. These current amplitudes and phases are converted to complex values, those values are divided by the voltage amplitude of the applied signal, and the resulting complex values are assembled into the vector of observed currents $$\left(\frac{I_n}{V_n}\right).$$

(In this preferred embodiment, the same voltage amplitude is used for all interrogation signals; however, it is possible to use a different voltage for each.) From the distribution of path lengths and the distribution of interrogation signal wavelengths, the coefficient matrix is assembled as described above. The linear system is then solved for the resistances and capacitances of each of the approximately 200 paths (100 resistance paths and 100 capacitance paths). The straight line path resistance and capacitance are noted for the electrode pair position in question. (In this preferred embodiment, the other values are not used.)

Having thus determined values for the resistance and capacitance of the straight line path for all of the selected electrode position pairs, an image is then constructed by back projection or by Fourier analysis.

Another Preferred Embodiment

Finite Element Approach

In another preferred embodiment, a finite element representation of the object to be imaged is first determined, having a predetermined number of nodes at selected positions on the exterior of the object, an additional predetermined number of nodes at selected positions in the interior of the object, and edges joining neighboring nodes. The determination of the number and positions of nodes and the choice of node pairs to be connected by edges is accomplished in accordance with methods that are well known to persons having ordinary skill in the art of finite element analysis of the electrical properties of two and three dimensional objects. Pairs of exterior nodes, preferably on generally opposite sides of the object, are selected for application of the interrogation signals, thus establishing a set of electrode position pairs. The number of pairs to be included in the set is at least sufficient to determine a linear system as described below.

For each electrode position pair, a set of path impedances is determined as follows: First, the desired number of interrogation frequencies is determined. This should be at least equal to twice the number of edges in the finite element grid, and optimally a larger number should be used in case any readings must be discarded on account of error, in case it is desired to select those frequencies that best optimize the conditioning of the coefficient matrix, or in case the geometry of the finite element grid turns out to be such that some edges are not adequately interrogated by fewer frequencies. Then the number of paths to be analyzed is determined; this should be at least twice the number of edges in the finite element grid. Next, the possible paths through the grid between the two electrode nodes are enumerated in order by path length. For smaller grids, this may be done by enumerating all possible paths and sorting them by length; for larger grids, the number of possible paths makes this impracticable, and Monte Carlo methods may be used, or methods may be applied to generate the possible paths in ascending order by length, where the grid topology lends itself to such methods. The result of this analysis will be a list of at least as many paths, ordered by path length, as required to produce a number of path lengths equal to the number of paths to be analyzed as previously determined. A pair of electrodes is then placed on the object at the predetermined positions, the interrogation signals are applied, and the amplitudes and phases of the resulting currents are recorded as before. A coefficient matrix is constructed as before from the predetermined path lengths and interrogation signal wavelengths, and the linear system is solved for the resistance and capacitance of each of the predetermined path lengths.

When the analysis described in the preceding paragraph has been completed for each of the predetermined electrode position pairs, another linear system is constructed in which each row represents the equation for one path, as follows:

$$R_{PATH} = \sum_{K} R_{EDGE},$$

where $R_{PATH}$ is the total resistance of the path, $R_{EDGE}$ is the resistance of a single one of the edges comprising the path, and K is the number of edges comprising the path. This linear system can then be solved for the resistances of the edges. Using the path capacitances determined for all the paths, the capacitances of the edges can be similarly determined, keeping in mind that serial capacitances combine as $$\frac{1}{C_{PATH}} = \sum_{K} \frac{1}{C_{EDGE}}.$$

It may be necessary to adjust the number of paths included in the system, and to determine which paths should be used assuming data has been taken for a sufficient number of paths to overdetermine the system, in such a way as to optimize the conditioning of the system and allow determination of values for all edges. Since this approach results in resistance and/or capacitance values for all edges in the finite element grid, it in effect directly produces what amounts to an image of the resistance or capacitance properties of the object.

Interrogation of Straight Line Path Using Resonant Frequency Signal

A further enhancement of the system and method described herein for estimating the magnitude of the current following a straight line path between two electrodes in its passage through a medium having multiple possible current paths involves the application of an interrogation signal of such a frequency that resonance is induced along the straight line path. It is well known that when an electrical signal is applied to a conductor at a frequency such that the length of the conductor is equal to or closely approximates one-half the wavelength of the signal in the medium of which the conductor is composed, or an integral multiple thereof, the conductor will resonate, radiating electromagnetic energy, and thereby causing its observed impedance to increase markedly at the resonant frequency as compared to its impedance at other frequencies. The quantity of energy radiated as electromagnetic energy depends, among other things, upon the amplitude of the signal applied to the conductor, which in turn is attenuated to the extent it encounters impedance in its passage through the conductor.

Figure 4:
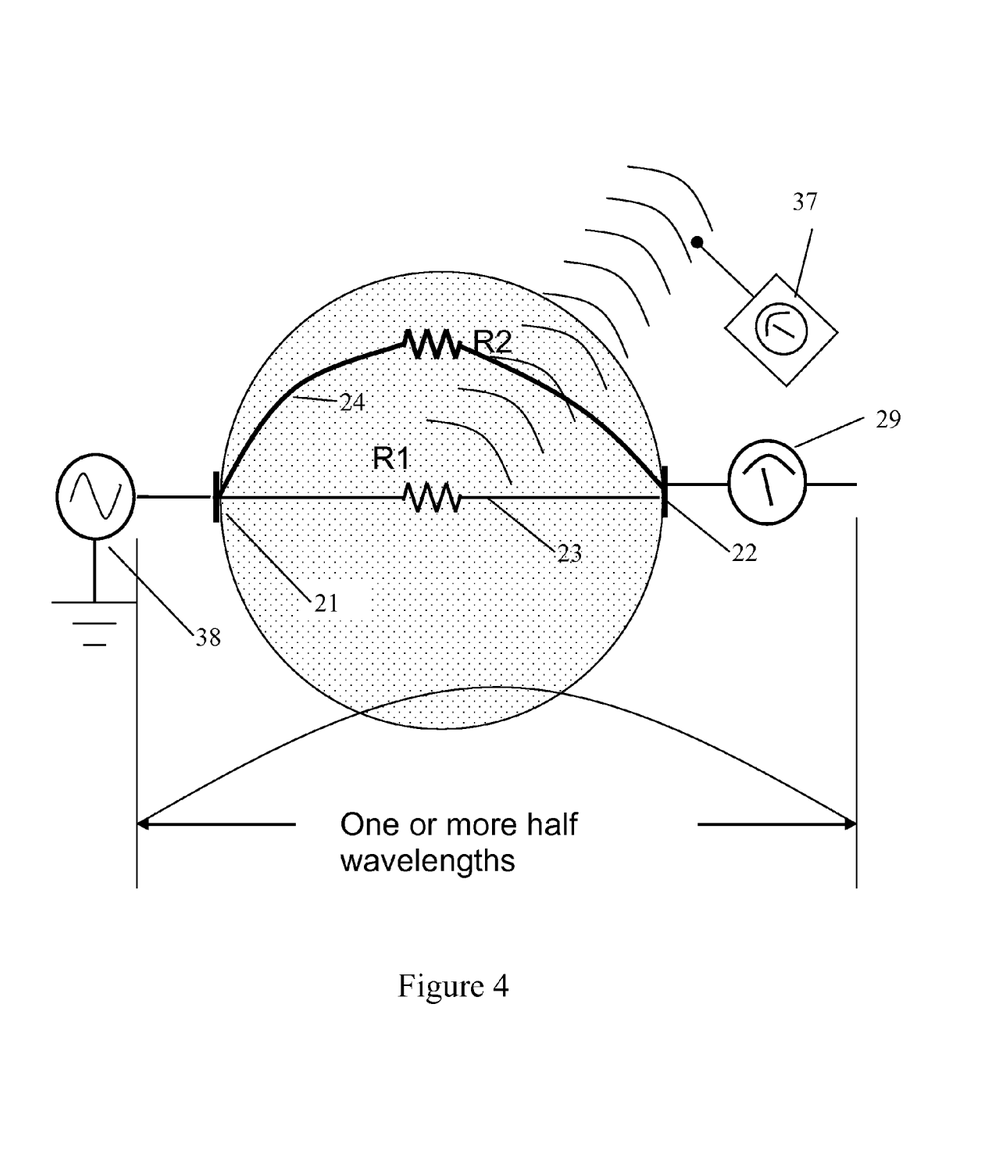
FIG. 4 illustrates a method for measuring impedance related properties of a conductive path through an object upon application of a signal resonating on the desired path.

Consider again the model previously described, in which the impedance properties of an object are represented as a resistance on a straight line path and one or more shunt resistances and/or capacitances on a longer path. As shown in FIG. 4, a signal generator 38 is used to apply a signal whose frequency is such that the half-wavelength of the signal is equal to the sum of the path length along the straight line path and the length of the conductor through which the signal is applied. The current will now be split between the straight line path 23 and the shunt path 24 in proportion to the respective impedances. However, the apparent impedance along the straight line path 23 will be greatly increased in comparison to the impedance that would be presented to a signal at a nonresonant frequency, because of the energy lost by electromagnetic radiation, while the apparent impedance along the shunt path 24 will not be increased. The magnitude of the radiation emitted from the resonant signal along the straight line path will depend in part upon the resistance and impedance properties of the medium of which the straight line 23 path is composed, since a more resistive medium will attenuate the amplitude of the signal as it passes down the conductor to a higher degree than a less resistive medium would. Therefore, the effect of the impedance properties of the conductive medium along the straight line path 23 will be relatively magnified in terms of their effect upon the observed impedance at resonance. It will be possible to improve the resolution of the determination of impedances using the system and method of the invention, by selecting interrogation frequencies each of which corresponds to a half-wavelength of which the straight line path or one of the predetermined shunt paths is an integral multiple, so that each path used in the analysis is interrogated by a signal that is resonant along such path.

It will also be possible to use this resonance effect directly to provide an imagable measure related to the impedance along the straight line path by measuring the amplitude of the electromagnetic field radiated at resonance. The amplitude of the electromagnetic field radiated from the resonating signal along the straight line path will be inversely related to the impedance properties of the medium comprising the path. In a preferred embodiment taking advantage of this effect, a plurality of electrode pair placements is first determined, in such a way that the plurality of straight line paths between the chosen electrode pair positions are spatially distributed in a manner suitable for image reconstruction by back projection when the impedances of such straight line paths have been determined. Then, for each electrode position pair so determined, electrodes 21, 22 are placed as illustrated in FIG. 4 and a signal generator 38 is used to apply an interrogation signal of predetermined amplitude and having a half-wavelength chosen so as to induce resonance in the straight line path 23 between electrodes through the object being measured. (This may be accomplished by applying a signal of whose half-wavelength the straight line path is an integral multiple, or, using a longer wavelength signal, by inducing resonance in the straight line path together with a conductor of predetermined length by which the signal is applied, as illustrated in FIG. 4. It will be possible to determine the correct frequency by beginning at a wavelength that is longer than that required to induce resonance along the straight line path; such a wavelength will instead induce resonance along some longer path through the object. The frequency will then be gradually increased while observing the intensity of the radiated signal. Since the straight line path is the shortest possible path, when the frequency is raised to a point such that the wavelength is slightly less than that required to induce resonance in the straight line path, no path will resonate, and the intensity of the radiated signal will abruptly decrease. In this way, the frequency required to induce resonance in the straight line path can be determined.) The intensity of the electromagnetic radiation so induced will then be measured using a field strength meter 37 or any other of the many methods known to persons having ordinary skill in the art of detecting and quantifying electromagnetic radiation. When such measurements have been made for each of the predetermined electrode position pairs, the set of measured intensities, each of which represents a measure of the impedance of the straight line path between the electrode pair to which it corresponds, will be used to generate an image of the impedance properties of the object by any of the well known methods for generating images from line integrals of physical properties of an object, such as back projection or Fourier analysis.

Method And Apparatus For Generating Images; Preferred Embodiment

Figure 5:
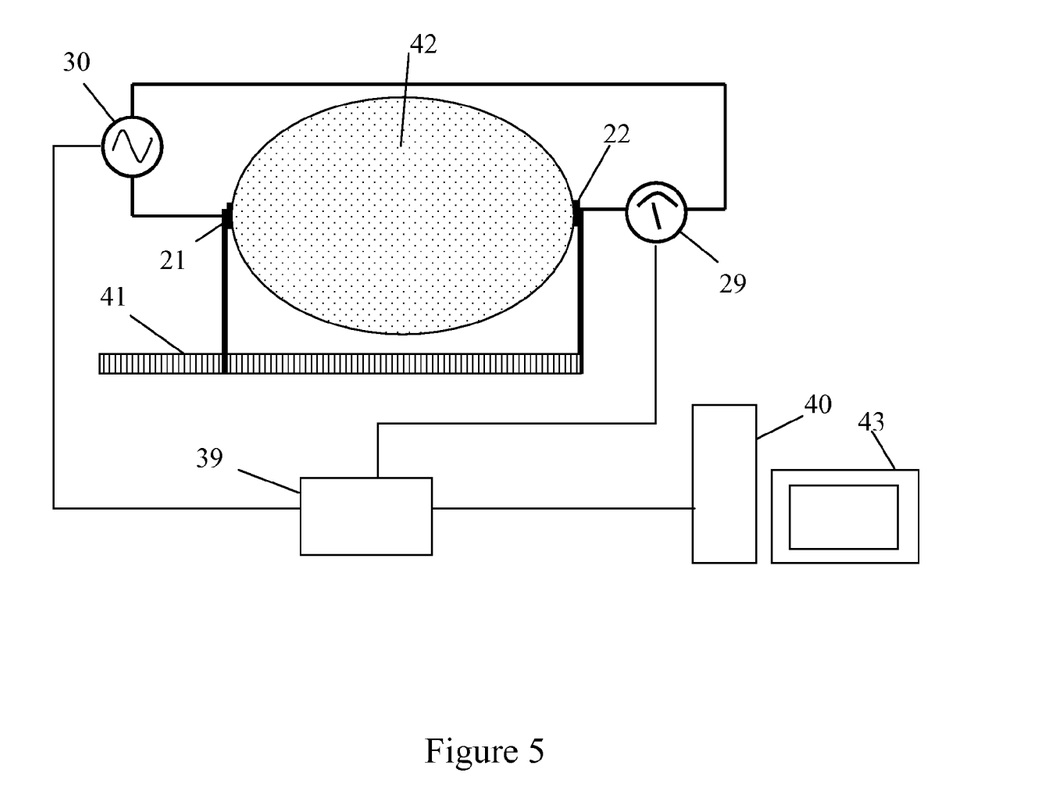
FIG. 5 illustrates an apparatus for measuring impedance related properties of an object.

Based on the system and methods described herein, an apparatus can be constructed for producing images. In a preferred embodiment, as shown schematically in FIG. 5, such an apparatus would comprise a signal generator 30 capable of generating interrogation signals at the desired amplitudes and frequencies; a set of electrodes 21 22 and leads; a caliper 41 for measuring the straight line distance between electrodes; an instrument 29 for measuring accurately the amplitude of the current at the downstream electrode and its phase relationship with the interrogation signal; an apparatus 39 for reporting the frequency, amplitude and phase of the interrogation signal and the amplitude and phase of the measured current signal and interfacing with a computer so as to report such data in a form useable by the computer; and a programmable computer 40 programmed to carry out the analysis described herein, to generate an image from the data so provided, and to display such image on a suitable display device 43 such as a monitor or printer.

The computations to be performed in connection with this invention may, of course, be incorporated in software and implemented on the hardware of a computer programmed in accordance with the methods described herein. The invention is intended to extend to the apparatus comprising a computer programmed to carry out the method of the invention, and to machine readable media upon which has been written or recorded a computer program for carrying out the method of this invention. The methods and apparatus of the invention may also be incorporated as part of an imaging apparatus for producing images representing the impedance properties of a sample by analyzing measurements taken between a plurality of electrode pairs using existing methods of producing an image from line integral measurements. Such methods are well known in the field of computed tomography. The invention is intended to extend to any such imaging apparatus incorporating the methods of the invention.

CONCLUSIONS, RAMIFICATIONS, AND SCOPE

The present invention is not limited in scope to the preferred embodiment or examples disclosed herein, which are intended as illustrations of one or a few aspects of the invention, and any methods that are functionally equivalent are within the scope of the invention. Various other modifications of the invention in addition to those shown and described herein will become apparent to those skilled in the art from the foregoing description. Such modifications are intended to fall within the scope of the invention.

In particular, it will be noted that the methods described do not necessarily require that the path whose impedance properties are measured be a straight line path, as long as the path is the shortest conductive path between the electrodes. The number of paths selected for analysis is not limited to the number described in the examples or preferred embodiments herein, and is limited only by the computational resources available and the ability to make accurate current amplitude and phase measurements for a sufficient distribution of interrogation frequencies; the larger the number of paths, the better the resolution obtained, other factors being equal. The selection of interrogation frequencies is not limited to the ranges described in the examples and preferred embodiments, and in principle any interrogation frequencies may be used provided that the wavelengths are not so short that the attenuation becomes too great for accurate measurement of currents. The interrogation signals are not necessarily limited to sinusoidal signals. Non-sinusoidal signals can be decomposed by Fourier analysis into a superposition of sinusoidal signals at specific frequencies in a manner well known to persons having ordinary skill in the art of signal processing. Such sinusoidal signals resulting from such decomposition can then be used to analyze the impedance properties of the object being imaged using the system and method described herein. It is therefore possible to apply a non-sinusoidal interrogation signal comprising a superposition of sinusoidal signals at two or more frequencies, measure the resulting current signal, decompose the current signal by Fourier methods into its component sinusoidal signals, and perform the analysis of impedance properties, using the system and method described herein, separately for each of the component sinusoidal signals. Although the interrogation signal is described in the examples and preferred embodiments herein as having a predetermined, fixed voltage amplitude, obviously the analysis can be carried out using a signal of fixed current amplitude and measuring the voltage signal produced, as will be apparent to a person having ordinary skill in the art of analyzing electrical signals. Although the examples and preferred embodiments discussed herein reflect the use of only two electrodes, it is possible to use an array of electrodes interrogated two at a time, provided that the straight line distance between electrode pairs is known or can be determined. Although the examples and preferred embodiments discussed herein reflect the supposition that the dimensions of the object, and therefore the straight line distances between electrodes, remains constant throughout the measurements, in the case of physiological measurements of regions such as the torso the dimensions may change due to breathing, movement, or for other reasons. It will be apparent upon inspection of the linear system describing the relationship between the measured currents and the path resistances and capacitances that it is merely necessary for the dimensions to remain constant during each single interrogation of a single electrode position pair at a single frequency, which can be accomplished nearly instantaneously. Although the examples and preferred embodiments discussed herein reflect the placement of electrodes on the outer surface of the object to be measured, the system and method described herein are equally applicable to configurations in which either electrode or both electrodes are placed at a point in the interior of the object. Doing so may make advisable the broadening of the range of assumed shunt path lengths, since the currents produced by the interrogation signals can then take less direct paths. Such configurations may be useful in geological applications where electrodes are placed in drilled holes, and in physiological measurement where electrodes are placed in the interior of the body by surgery, via a needle, or otherwise.

It is not required that the signals used to interrogate the object be electrical signals; the system and method described herein is applicable to any type of signal characterized by wave-like propagation through an attenuating medium through which the signal tends to follow paths of least resistance, including, without limitation, acoustic signals.

It must be recognized that the measurements described herein may not necessarily provide exact straight line impedance values due to a variety of factors, not least of which is that a straight line has, by definition, infinitesimal thickness and therefore infinite impedance. The system and method discussed herein produces a reasonable measure related to the impedance along paths of finite thickness, corresponding to a resolution that can improved to an arbitrary extent by increasing the number of interrogation frequencies. The values produced by the methods described will, however, bear a relation to physiological properties, including impedance, and/or some composite thereof, and provide quantities that can usefully be employed to produce images that furnish information relevant to assessment of physiological states. Therefore, even to the extent that the values produced are not, strictly speaking, precisely accurate straight line impedance values, they can be used to produce images that themselves are useful.

APPENDIX A

Mathematica Code Illustrating Computation of Specific Example with 3 Resistance and 3 Capacitance Paths Corresponding to FIG. 2

```
1. Computation
(* this file contains the calculations for a n-
  path RC network. It is intended to be used with the accompanying file
    EITnpathfns.nb which contains many of the functions used herein,
so as to avoid clutter.  *)
npaths = 3; (* each has an R and a C branch so actual no of paths is twice this *)
(* path table is generated randomly using pathr fn and output copied here so
  that it stays the same on recalculation*)
path = {{{15.3235, 46.2676}
  {{25.0759, 113.762}, 1.42838}}
{{{15.3235, 46.2676}, 1}, {{23.4823, 138.293}, 1.29172}, {{25.0759, 113.762}, 1.92838}}
(* wavelengths of signals to be used for interrogating (arbitrary) *)
sep = .09;
lambdas = Table[1 + (i − 1) * sep, {i, 1, 2 * npaths}]
{1 , 1.09, 1.18, 1.27, 1.36, 1 . 45}
(* generate matrix of the path currents at the various interrogation
    frequencies. Row corresponds to frequency, column corresponds to path,
  in order R, C, in increasing length. *)
iin = Table[ilist[pathcc[path, lambdas[[i]]], 10, lambdas[[i]]], {i, 1, Length[lambdas]}]
{{0.652592, 0.581416 i, −0.110357+ 0.411305 i,
    −1.67847 − 0.450349 i, −0.359088 + 0.17346 i, −0.621818 − 1.28726 i },
  {0.566723 − 0.323578 i, 0.269482 + 0.963222 i, 0.168969 + 0.390896 i,
    −1.46348 + 0.632602 i, −0.147829 + 0.370377 i, −1.2181 − 0.486181 i },
  {0.375102 − 0.534018 i, 0.403198 + 0.283212 i, 0.352698 + 0.238652 i,
    −0.82534 + 1.21975 i , 0.0979815 + 0.386565 i, −1.17937 + 0.297669 i ),
  {0.151952 − 0.634655 i, 0.445229 + 0.106598 i, 0.423396 + 0.045673 i,
    −0.146759 + 1.36049 i , 0.282502 + 0.28147 i , −0.799996 + 0.79741 i },
  {−0.0602136 − 0.649809 i, 0.425688 − 0.0394958 i, 0.904839 − 0.13212 i,
    0.396441 + 1.21477 i , 0.379054 + 0.123898 i, −0.32658 + 0.999139 i },
  (−0.241549 − 0.606243 i, 0.372998 − 0.148417 i, 0.329556 − 0.26971 i,
    0.759067 + 0.927494 i, 0.397041 − 0.0373057 i , 0.0922298 + 0.981591 i}}
(* i0 is vector of observed currents at each of the interrogation frequencies,
    which is the superposition of the path currents for all paths  *)
i0 = Table[iout[iin[[i]]], {i, 1, Length[iin]}]
{−2.11715 − 0.571424 i, −1.82923 + 1.04734 i, −0.770728 + 1.89183 i,
  0.361819 + 1.95698 i, 1.21923 + 1.51644 i, 1.70884 + 0.847409 i}
(* pull out separate vector of pathlengths from paths *)
plengths = Transpose[pathcc[path, 1]] [[2]]
{1, 1, 1.29172, 1.29172, 1.42838, 1.42838}
(* make rotation matrix -- element R[a,b] is the carplex unit vector which
    when multiplied by a signal shifts the phase of that signal by the amount
    of the phase shift that would be observed for a signal of wavelength a
    measured at a point at a distance b from the point of application of the
    signal.  In the case of the capacitance paths,
  R[a,b] is scaled by 2*Pi*(200000000/lambda)*(1/1000000000000) to account
    for the dependence of capacitive reactance on frequency,
    the assumed speed of light in the medium,
    and to allow capacitances to be expressed in picofarads,
    and multiplied by I to account for the 90 degree phase shift on a capacitance path.  *)
R = mrot[plengths, lambdas]
{{1., 0.00125664 i , −0.259143 + 0.965839 i,
    −0.00121371 − 0.000325648 i, −0.900446 + 0.434967 i, −0.000546596 − 0.00113153 i},
  {0.868417 − 0.495834 i, 0.000571636 + 0.00100118 i, 0.396778 + 0.917915 i,
    −0.00105824 + 0.000457436 i, −0.370696 + 0.928754 i, −0.00107074 − 0.000427367 i },
  {0.574787 − 0.818303 i , 0.000871449 + 0.000612118 i, 0.828216 + 0.560409 i,
    −0.000596805 + 0.000882006 i, 0.245697 + 0.969347 i , −0.0010323 + 0.000261655 i},
  {0.232844 − 0.972514 i , 0.000962281 + 0.000230394 i, 0.994232 + 0.107251 i,
    −0.000106122 + 0.000983771 i , 0.7084 + 0.705811 i, −0.000698385 + 0.000700946 i },
  {−0.0922684 − 0.995734 i, 0.000920056 − 0.0000852558 i, 0.950656 − 0.310247 i,
    0.000286668 + 0.000878404 i, 0.950513 + 0.310686 i, −0.000287073 + 0.000878272 i },
  {−0.370138 − 0.928977 i, 0.000805094 − 0.000320779 i, 0.773872 − 0.633342 i,
    0.000548883 + 0.000670673 i, 0.995615 − 0.0935475 i, 0.0000810726 + 0.000862846 i}}
(* now should be able to solve the linear system i=v*R.sigma for sigmas *)
Chop[LinearSolve[10* R, i0], 10^−7]
{0.0652592, 46.2676, 0.0425853, 138.293, 0.0398789, 113.762}
(* which returned the exact capacitances we started with and the reciprocals
``` of the resistances. *)
2. Mathematica functions required for computation in (1) above
(* each path is a {R,C} and a length in that order,
  here sort of randomly chosen but in increasing lengths. We will use base
  freq of 200 Wz corresponding to wavelength of 1M at a c of 2 E8 m/sec,
  and resistances on the order of 10 ohms, capacitances on the order of 100 pf,
  giving currents on the order of 1 A *)
pathr[n_] :=
  Module[{i, p},
   p=
    Table[{{Random[Real, {(i − 1) * 10, (i + 1) * 10}], Random[Real, {(i − 1) * 50, (i + 1) * 50}]},
      Random[Real, {.9 + (i − 1) * .2, 1.1 + (i-1) * .2}]}, {i, 1, n}];
   p[[1, 2]]= 1;
   p
  ]
pathr[3]
{{{10.5161, 83.9719}, 1}, {{29.6562, 136.392}, 1.13124}, {{25.4662, 123.823}, 1.32228}}
(* convert a signal given as an amplitude and phase to polar form *)
z[amp_, phase_]:= Module[{x, y},
   x = amp* Cos [phase];
   y = amp* Sin [phase];
   x + I * y
  ]
(* path complex conductivity as function of wavelength, path length, and R and C *)
sigma[r_, c_, lambda_]:=
  Module[{i}, 1/r + I * (2*Pi * (200000000/ lambda) * (c/1000000000000))
  ]
(* from a path expressed as {{{R ohms, C pf}, pathlength in meters} . . . }
  generate a path table that treats the R and C as separate paths,
  at a specified reference wavelength lambda,
  each element of the new path expressed as {complex conductivity, length} *)
pathcc[path_, lambda_] := Module[}pt},
   pt = Table[{{Re[sigma[path[[i, 1, 1]], path[[i, 1, 2]], lambda]], path[[i, 2]]},
     {I * Im[sigma[path[[i, 1, 1]], path[[i, 1, 2]], lambda]], path[[i, 2]]}},
     {i, 1, Length[path]56 ];
   Flatten[pt, 1]
  ]
(* given an angle_ in radians,
  generate a complex number of phase equal to angle_ and amplitude 1
   (which can be multiplied by any other complex number to rotate its phase
    by angle_)  *)
unitz[angle_]:= Module[{ },
   imz = Sin[angle];
   rez = Cos[angle];
   N[(rez + I * imz)]
  ]
(* given a path length plen_ and a wavelength lambda_,
  generate a unit complex rotation factor corresponding to the phase shift
   caused by the path length difference -- i.e. applying a signal of wavelength lambda,
   what is the phase of that signal at a distance plen from the point of application *)
zrot[plen_, lambda_] := Module[{ },
   Chop [unitz[((plen − lambda) / lambda) * 2*Pi]]
  ]
(* given a set of path lengths and a set of interrogation wavelengths,
  generate a rotation matrix of which the rows correspond to the interrogation
   wavelengths, the columns correspond to the path lengths in order R, C,
   R, C . . . in increasing length,
  and each element mrot[a,b] is the complex unit vector which when multiplied
   by a signal shifts the phase of that signal by the amount of the phase
   shift that would be observed for a signal of wavelength a measured at
   a point at a distance b from the point of application of the signal.  *)
mrot[plens_, lambdas_] := Module[{i, j, temp},
   temp = Table[Table[zrot[plens[[i]], lambdas[[j]]]], {i, 1, Length[plens]}],
     {j, 1, Length[lambdas]}];
   For[j = 1, j ≦ Length[lambdas], j++,
    For[i = 2, i ≦ Length[plens], i += 2,
     temp[[j, i]] *= I * 2 * Pi * (200000000 / lambdas[[j]]) * (1 / 100000000000);
    ];];
   temp
  ]
(* This returns the phase angle of a signal expressed in polar form. The
  problem with arctan is that tan is the same in first and third quadrants
  and in second and fourth. Therefore need to distinguish based on actual
  sign of both Re and Im.  *)
phasefn[zin_] := Module[{ },
   If[Re[zin] == 0 && Im[zin] >0, Return[Pi/2],];
   If[Re[zin] == 0 && Im[zin] <0, Return[3 Pi/2],];
   If[Re[zin] ≧ 0,
    If[Im[zin] ≧ 0,
     ArcTan[Im[zin] / Re[zin]], -continued

```
            2 * Pi + ArcTan[Im[zin] / Re[zin]]],
        If[Im[zin] ≧ 0,
            Pi + ArcTan[Im[zin] / Re[zin]],
            Pi + ArcTan[Im[zin] / Re[zin]]]
        ]
]
(* generate current signals in polar form for each path for an applied
   signal of voltage v and wavelength lambda, based on path resistance and length,
   using a table of paths in the form generated by fn pathcc. Note there is
   no need to treat capacitances differently because the impedances are
   already rotated by expressing than as imaginary in the path list created
   using pathcc.  *)
ilist[path_, v_, lambda_] := Module[{i},
    Chop[Table[v*path[[i, 1]]*zrot[path[[i, 2]], lambda], {i, 1, Length[path]}]]
]
(* resultant current signal of a list of superposed signals *)
iout[ilist_] := Module[{i},
    Sum[ilist[[i]], {i, 1, Length[ilist]}]
]
```

I claim:

1. An apparatus for estimating the impedance properties along a shortest-distance path between two points separated by conductive medium offering at least two conductive paths between such points, comprising:
   a pair of electrodes for introducing alternating electrical signals between said two points;
   a signal generator for applying alternating electrical signals between said pair of electrodes at at least two frequencies;
   a detector for measuring the amplitudes and phases of said signals upon their passage through said conductive medium between said two points; and
   a computer programmed to compute, from the length of said shortest-distance path and said amplitudes and phases of said signals, a measure of the impedance properties of said shortest-distance path.

2. The apparatus of claim 1, wherein said amplitudes and phases comprise current amplitudes and phases.

3. The apparatus of claim 1, wherein said amplitudes and phases comprise voltage amplitudes and phases.

4. The apparatus of claim 1, wherein said signals comprise signals that are propagated ionically.

5. The apparatus of claim 1, wherein said shortest-distance path comprises a straight line path between said two points.

6. The apparatus of claim 1, further comprising a caliper for measuring the straight line distance between said two points.

7. The apparatus of claim 1, wherein said measure of the impedance properties of said shortest distance path is an estimate of the amplitude of the portion of at least one of said signals passing along said shortest distance path.

8. The apparatus of claim 1, wherein said measure of the impedance properties of said shortest distance path is an estimate of electrical impedance along said shortest distance path.

9. An apparatus for determining a spatial distribution of impedance properties within a conductive medium, comprising:
   electrodes for introducing alternating electrical signals between a plurality of pairs of points, there being at least a shortest distance conductive path and a second conductive path through said conductive medium between each said pair of points;
   a signal generator for applying alternating electrical signals between each said pair of points at least two frequencies;
   a detector for measuring the amplitudes and phases of said alternating electrical signals upon their passage through said conductive medium between each said pair of points; and
   a computer programmed to compute, from the lengths of said shortest-distance paths between said pairs of points and the changes in amplitude and phase of said alternating electrical signals upon their passage through said conductive medium, a measure of the impedance properties of the shortest-distance path between each said pair of points, and from said measures of impedance properties of said shortest distance paths, an estimate of a spatial distribution of a measure of impedance properties within said conductive medium.

* * * * *